(12) United States Patent
Turchetta et al.

(10) Patent No.: US 8,236,817 B2
(45) Date of Patent: Aug. 7, 2012

(54) POLYMORPHS OF 1-CYCLOPROPY1-7-([S,S])-2,8-DIAZADICYCLO[4.3.0]NON-8-YL)-6-FLUORO-1,4-DIHYDRO-8-METHOXY-4-OXO-3-QUINOLINE CARBOXYLIC ACID HYDROCHLORIDE AND METHODS FOR THE PREPARATION THEREOF

(75) Inventors: Stefano Turchetta, Rome (IT); Pietro Massardo, Rome (IT); Valentina Aromatario, Rome (IT)

(73) Assignee: Chemi S.p.A., Cinisello Balsamo (MI) (IT)

( * ) Notice: Subject to any disclaimer, the term of this patent is extended or adjusted under 35 U.S.C. 154(b) by 703 days.

(21) Appl. No.: 10/580,173

(22) PCT Filed: Oct. 28, 2004

(86) PCT No.: PCT/EP2004/052699
§ 371 (c)(1),
(2), (4) Date: May 22, 2006

(87) PCT Pub. No.: WO2005/054240
PCT Pub. Date: Jun. 16, 2005

(65) Prior Publication Data
US 2007/0072895 A1    Mar. 29, 2007

Related U.S. Application Data

(60) Provisional application No. 60/532,779, filed on Dec. 24, 2003.

(30) Foreign Application Priority Data

Nov. 20, 2003  (IT) .............................. MI2003A2259

(51) Int. Cl.
*A61K 31/47* (2006.01)
*C07D 471/04* (2006.01)
(52) U.S. Cl. ........................................ 514/300; 546/113
(58) Field of Classification Search .................. 546/113; 514/300
See application file for complete search history.

(56) References Cited

U.S. PATENT DOCUMENTS

| 5,607,942 | A | | 3/1997 | Petersen et al. | |
| 5,849,752 | A | * | 12/1998 | Grunenberg et al. | 514/300 |
| 6,627,646 | B2 | * | 9/2003 | Bakale et al. | 514/322 |
| 2006/0264635 | A1 | | 11/2006 | Satyanarayana et al. | |

FOREIGN PATENT DOCUMENTS

| EP | 0 550 903 A1 | 7/1993 |
| EP | 0 780 390 A1 | 6/1997 |
| JP | 05-271229 | 10/1993 |
| JP | 07-126266 | 5/1995 |
| WO | WO 03/049688 A2 | 6/2003 |
| WO | WO 2004/091619 A1 | 10/2004 |

OTHER PUBLICATIONS

Chemical & Engineering News, Feb. 2003, 32-35.*
Brittain ed., "Polymorphism, etc.," NY: Marcel Dekker, Inc., 1999, 1-2, 183-226.*
US Pharmacopia #23, National Formulary #18, 1995, 1843-1844.*
Muzaffar et al.,"Polymorphism and Drug Availability, etc.," J of Pharm. (Lahore), 1979, 1(1), 59-66.*
Jain et al., "Polymorphism in Pharmacy", Indian Drugs, 1986, 23(6) 315-329.*
Taday et al., "Using Terahertz, etc.," J of Pharm. Sci., 92(4), 2003, 831-838.*
Concise Encyclopedia Chemistry, NY: Walter de Gruyter, 1993, 872-873.*
Rowland et al., "Clincial Pharmacokinetics. etc.," 1995, p. 123.*
Silverman, The Organic Chemistry of Drug Design and Drug Action, NY: Academic Press, 1993, 72-76.*
Ulicky et al., Comprehensive Dictionary of Physical Chemistry, NY: Prentice Hall, 1992, p. 21.*
Doelker, english translation of Ann. Pharm. Fr., 2002, 60:161-176, pp. 1-39.*
Doelker, english translation of S.T.P. Pharm Pratiques (1999), 9(5), 399-409, pp. 1-33.*
Otsuka et al., "Effect of Polymorphic Forms, etc.," Chem. Pharm. Bull., 47(6) 852-856 (1999).*
CMU Pharmaceutical polymorphism, internet, p. 1-3 (2002) (print out Apr. 3, 2008).*
Singhal et al., "Drug Polymorphism, etc.," Advanced drug delivery reviews 56, p. 335-347 (2004).*
Brittain ed., "Polymorphism, etc.," NY:Marcel Dekker, Inc., 1999, 235-238.* Bernstein et al., "Polymorphism in Molecular Crystals", Oxford: Clarendon Press, 2002, pp. 117, 118 and 272.*
Davidovitch et a., "Dectection of Polymorphism, etc.," American Pharmaceutical Review, IN: Russell Pub., 2004, 7(1), pp. 10, 12, 14, 16 and 100.*

* cited by examiner

*Primary Examiner* — Patricia Morris
(74) *Attorney, Agent, or Firm* — Lucas & Mercanti, LLP

(57) ABSTRACT

Two novel crystalline forms, designated form A and form B of the antibacterial agent 1-cyclopropyl-7-(S,S)-2,8-diazabicyclo[4.3.0]non-8-yl)-6-fluoro-1,4-dihydro-8-methoxy-4-oxo-3-quinoline carboxylic acid hydrochloride of formula, the preparation thereof, and their pharmaceutical compositions are described. These crystalline forms, which are characterized by greater ability and ease of preparation and of formulation, can be produced by industrially applicable methods which comprises the steps of: a) suspending 1-cyclopropyl-7-(S,S)-2,8-diazabicyclo-[4.3.0]non-8-yl)-6-fluoro-1,4-dihydro -8-methoxy-4-oxo-3-quinoline carboxylic acid hydrochloride in a solvent selected from an alcohol and a polyalcohol, b) heating the mixture under reflux, c) cooling, d) isolating the product which is separated, (form A) and, additionally, e), reslurrying the solid at reflux in a solvent selected from alcohols and polyols or mixtures thereof, in which the resulting mixture has an overall water content of between 2.5% and 0.01% by weight, f) isolating the product (form B).

16 Claims, 8 Drawing Sheets

US 8,236,817 B2

POLYMORPHS OF 1-CYCLOPROPY1-7-([S,S])-2,8-DIAZADICYCLO[4.3.0]NON-8-YL)-6-FLUORO-1,4-DIHYDRO-8-METHOXY-4-OXO-3-QUINOLINE CARBOXYLIC ACID HYDROCHLORIDE AND METHODS FOR THE PREPARATION THEREOF

This application is the U.S. National Phase of International Application PCT/EP2004/052699, filed 28 Oct. 2004, which designated the U.S. PCT/EP2004/052699 claims priority to Italian Application No.MI2003A002259 filed 20 Nov. 2003 and U.S. Provisional Application No. 60/532,779 filed 24 Dec. 2003. The entire content of these applications are incorporated herein by reference.

FIELD OF THE INVENTION

The present invention relates to two novel polymorphs of 1-cyclooroyl-7-(S,S)-2,8-dlazabicyclo[4,3,0]-non-8-yl)-6-fluro-1,4dihydro-8-methoxy-4-oxo-3-quinoline carboxylic acid hydrochloride, the methods for the preparation thereof, and pharmaceutical formulations which include them.

STATE OF THE ART 1-cyclopropyl-7-(S,S)-2,8-diazabicyclo[4.3.0]non-8-yl)-6-fluoro-1,4-dihydro-8-methoxy-4-oxo-3-quinoline carboxylic acid hydrochloride, also known by the name moxifloxacin hydrochloride, is an antibacterial agent of formula: which is widely used therapeutically in the treatment of infections by antibiotic-resistant bacteria.

Its preparation is reported in EP550903 and the preparation and characteristics of its monohydrate pseudopolymorph are described in U.S. Pat. No. 5,849,752. It is clear from this patent that the only known forms of moxifloxacin hydrochloride are the anhydrous form and the monohydrate, extensive identifying documentation of which is provided. In the patent, it is also written that the anhydrous form of the active ingredient is unsuitable for the preparation of pharmaceutical formulations since it absorbs water from the atmosphere. The monohydrate form, on the other hand, does not have the disadvantage of being hygroscopic and can be prepared in the form of crystalline prisms, which confer on the powder characteristics of fluidity that are advantageous for formulation purposes, or in the form of needles which tend rather to clump together.

According to the US patent, the monohydrate in prism form can be produced by suspending moxifloxacin hydrochloride in ethanol/water mixtures containing up to 10% of water whereas, to form the monohydrate in needle form, water or any water/alcohol mixture with a water content greater than 10% may be used. It is also mentioned in the description of the invention that, in order to produce the monohydrate form, the relative humidity value should not fall below 30% during the drying stage, since this condition would lead to the formation of the anhydrous form. However, the examples of the preparation of moxifloxacin hydrochloride monohydrate given in U.S. Pat. No. 5,849,752 show serious limitations of industrial applicability both owing to the large volumes of solvent that are used and owing to the subsequent production technique.

In fact the method provides first of all for the anhydrous form of moxifloxacin hydrochloride to be dissolved in a large quantity of solvent and then for the solvent to be evaporated completely so that the active ingredient is recovered as the evaporation residue. However, if this evaporation to dryness is performed hot, for example, by heating to 60-70° C., it may lead to degradation of the product whereas, if it is performed spontaneously at room temperature as described in Examples 5 and 6 of the US patent, it requires very long periods of time that are not practicable industrially.

In conclusion, there is at the moment still a need to identify an industrially applicable method of producing a stable and easily formulated form of moxifloxacin hydrochloride which does not require laborious stages for the evaporation of large volumes of solvent and which is sufficiently quick and gentle not to lead to alterations in the final product.

DESCRIPTION OF THE INVENTION

The subjects of the present invention are therefore two novel, stable, and easily formulated crystalline forms of moxifloxacin hydrochloride, a method for the preparation thereof, and pharmaceutical formulations, which include them.

It has in fact surprisingly been found that, by means of an easily industrially applicable method, which comprises the steps of:
a) suspending moxifloxacin hydrochloride in a suitable solvent,
b) heating the mixture under reflux,
c) cooling, and
d) isolating the product which is separated, a novel hydrated crystalline form of moxifloxacin hydrochloride, which is stable and easy to formulate, designated as moxifloxacin hydrochloride form A is obtained.

Further, by subjecting the product resulting form the above step d) to the following additional stages characterized by
e) reslurrying the solid in a suitable solvent, and
f) isolating the product,
another novel form of moxifloxacin hydrochloride, named form B, stable and easy to formulate too, is prepared.

The starting moxifloxacin hydrochloride may be either in amorphous form or in any crystalline form, for example, in anhydrous or monohydrate crystalline form, as described in U.S. Pat. No. 5,849,752. Preferably, the starting moxifloxacin hydrochloride is an anhydrous form having a water content of less than 0.3%.

The solvent used in the method described above is generally an alcohol or a polyol, preferably a $C_1$-$C_6$ alcohol or polyol, for example, methanol, ethanol, isopropanol, n-propanol, n-butanol, isobutanol, terbutanol, n-pentanol, n-hexanol, 1,2-ethandiol, 1,2-propandiol, 1,3-propandiol, methoxyethanol, methoxypropanol, etc. . . . , most preferably ethanol or isopropanol, or mixtures thereof.

In particular, the novel crystalline forms of moxifloxacin hydrochloride can be produced, in accordance with the above-described steps, by the suspension of moxifloxacin hydrochloride in the preselected solvent, provided that the resulting mixture has an overall water content of between 2.5% and 0.01% by weight. "Overall water content" means the quantity of water resulting from the sum of the water content of the starting moxifloxacin hydrochloride and of the water contained in the solvent.

Preferably, a solvent with a water content of between 1% and 0.01%, more preferably between 0.3% and 0.01%, and even more preferably between 0.1 and 0.01% is used. The production of these novel crystalline forms is particularly surprising in the light of the misleading teaching provided by the patent U.S. Pat. No. 5,849,752; in fact in the description thereof (col. 2, lines 62-65) it is stated that "the preferred monohydrate form in the form of prisms can be obtained by suspending the crystalline anhydrous product in ethanol/water mixtures, particularly in the said mixtures with a maximum water content of 10%", thus meaning also mixtures with 2.5%, 1% or 0.1% of water. In fact, in these conditions, it has surprisingly been found that, instead of the prism form described by the US patent, form A or, following the additional steps e)-f), form B, which are the subject of the present invention, are obtained.

In the method for the preparation of form A, the solvent is generally used in a ratio of between 50:1 and 2:1, preferably between 30:1 and 5:1, more preferably about 10:1, the ratio being expressed as ml of solvent per gram of moxifloxacin hydrochloride.

The mixture of moxifloxacin hydrochloride and solvent is kept under reflux (step a) for a variable period of time which will depend on various factors such as, for example, the type of solvent, the form of the starting product, the total quantity of water, etc., and is preferably at least 1 hour, more preferably about 4 hours.

The cooling of the mixture (step b) may be spontaneous or accelerated by appropriate means known to a person skilled in the art. The mixture may be cooled to room temperature or cooling may continue to lower temperatures; in general, it is preferred to allow the mixture to cool spontaneously until room temperature is reached.

In a particularly preferred method, cooling to room temperature takes place in about 2 hours and the mixture is allowed to rest at that temperature for a further 2 hours before the isolation is performed.

The novel crystalline forms according to the invention are isolated (step d and f) by conventional techniques, for example, by filtration, decantation or centrifuging.

BRIEF DESCRIPTION OF THE DRAWINGS

The invention will now be described in more detail with reference to the accompanying drawings, in which.

Figure 1:
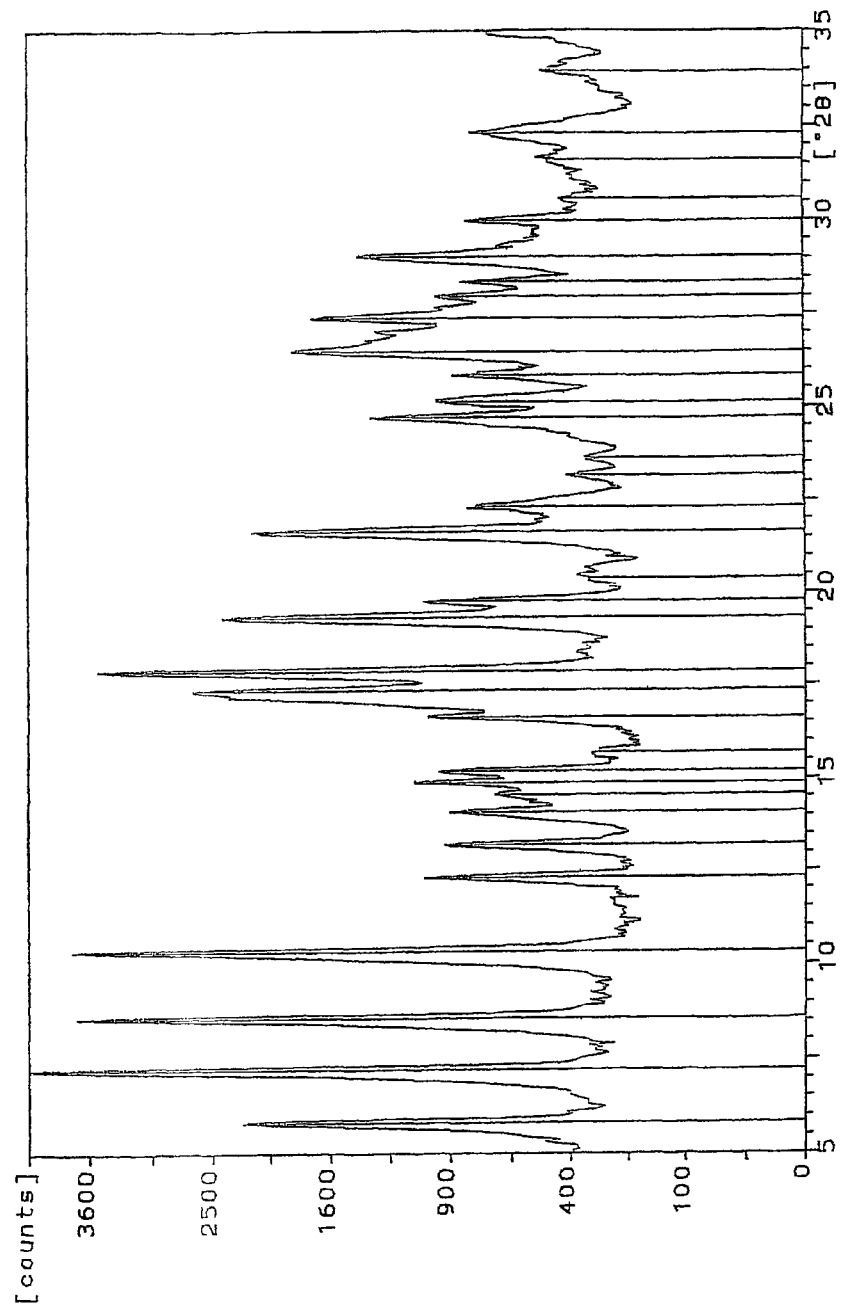
FIG. 1 is an X-ray diffraction spectrum (XRD) of the crystalline form A of moxifloxacin hydrochloride.
Figure 2:
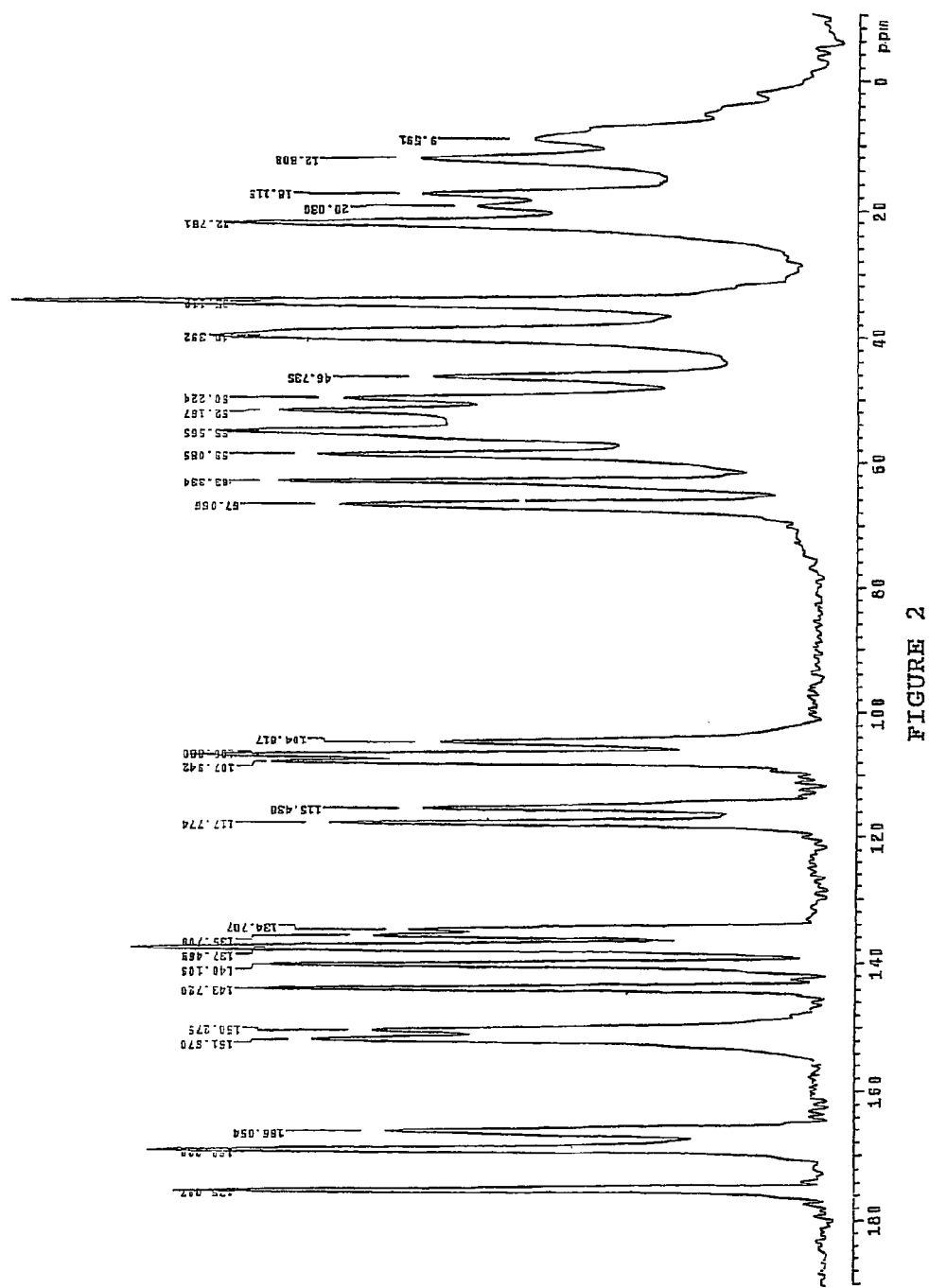
FIG. 2 is a solid state carbon-13 NMR spectrum of the crystalline form A of moxifloxacin hydrochloride.
Figure 3:
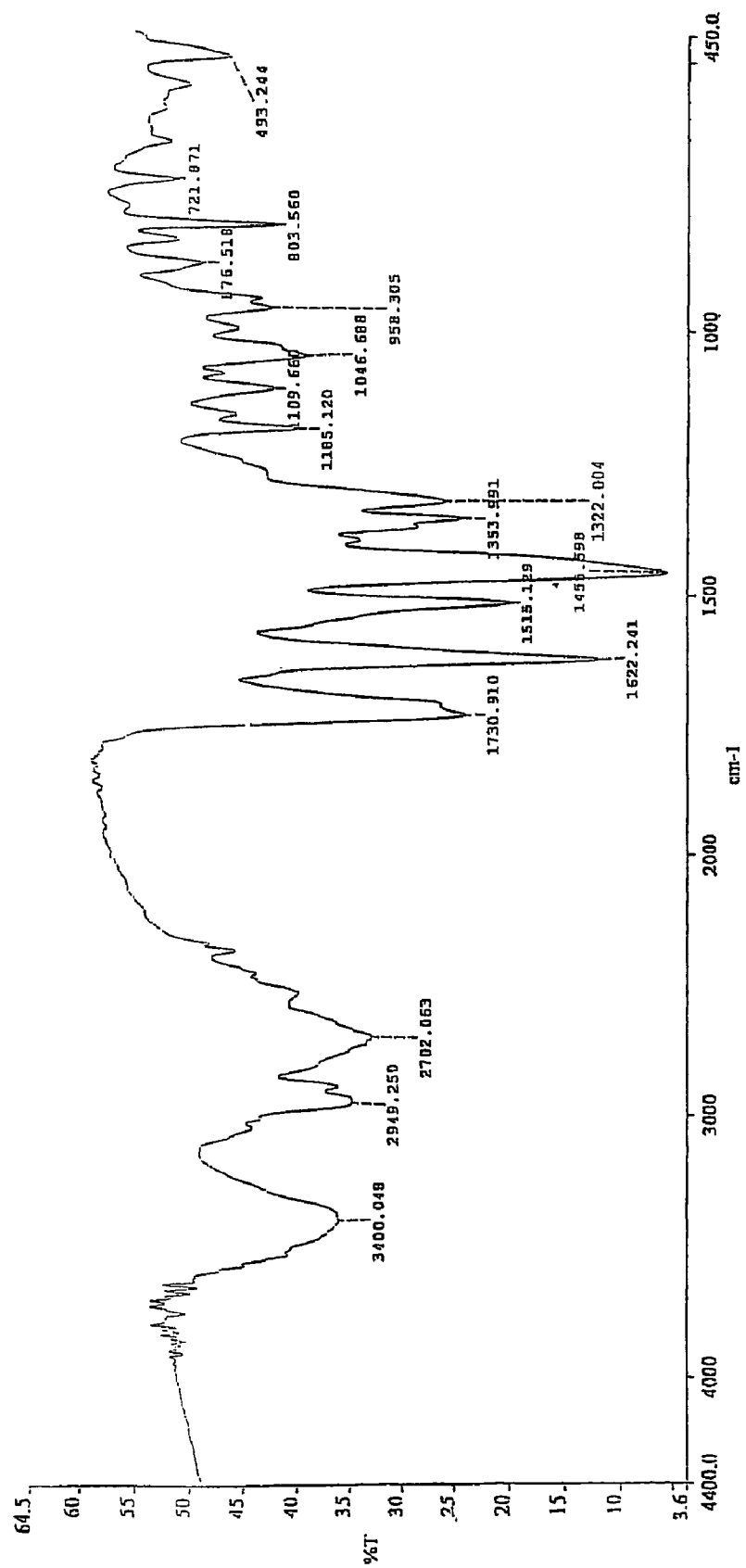
FIG. 3 is an infrared spectrum of the crystalline form A of moxifloxacin hydrochloride.
Figure 4:
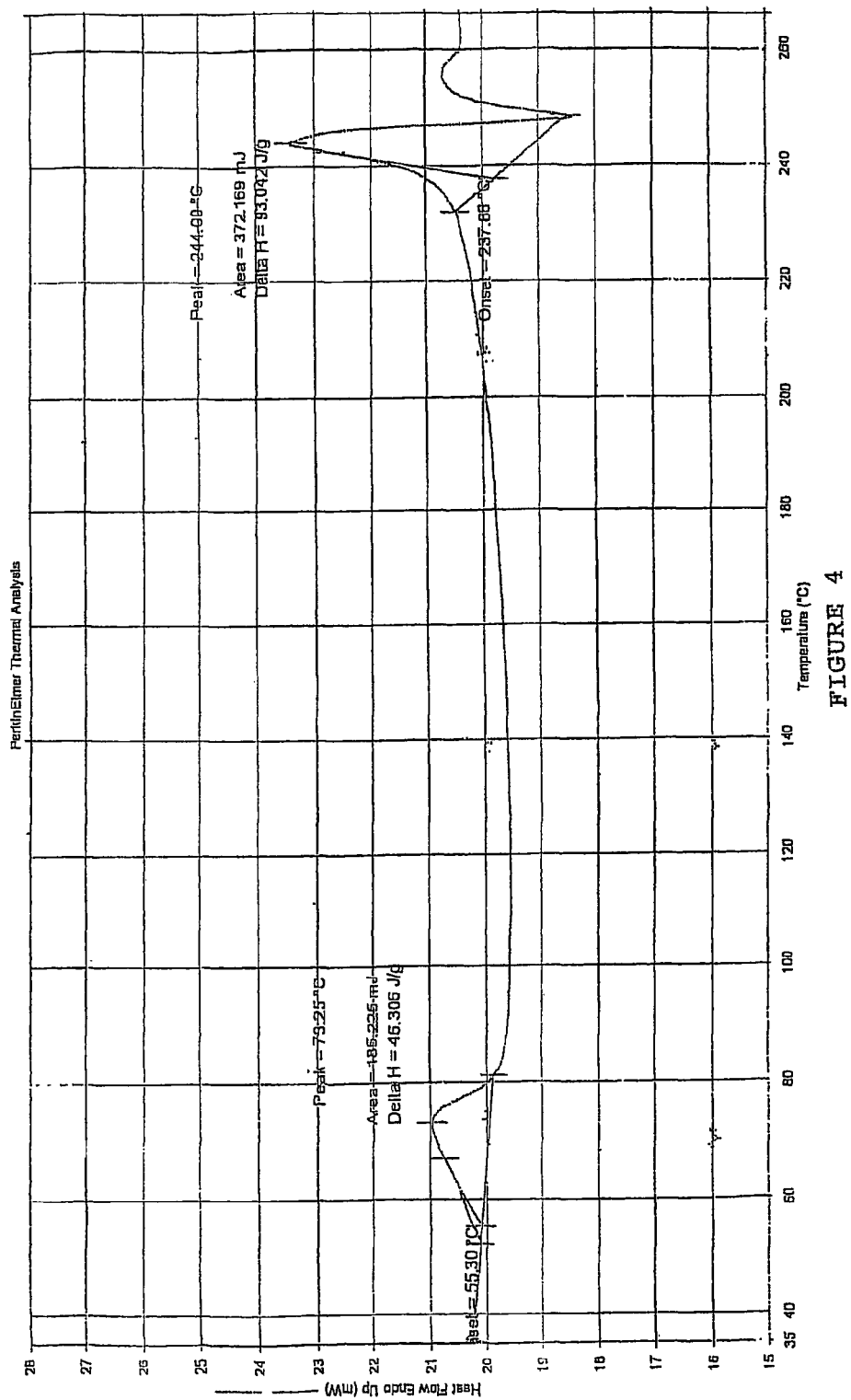
FIG. 4 is a DSC trace of the crystalline form A of moxifloxacin hydrochloride.

The novel crystalline form A of moxifloxacin hydrochloride is characterized by the X-ray diffraction spectrum (XRD) which is shown in FIG. 1 and described in Table 1, by the solid-state $^{13}$C-NMR spectrum which is shown in FIG. 2 and tabulated in Table 2, by the IR spectrum which is given in FIG. 3, and by the DSC trace which is shown in FIG. 4. The differences in comparison with the known forms can clearly be distinguished by comparing this spectral data with that of the anhydrous and monohydrate forms described in U.S. Pat. No. 5,849,752. In particular, in the XRD spectrum of the novel form, characteristic peaks are situated at 7.2, 12.3, 16.6 and 21.6 are distinguished and, in the solid-state $^{13}$C-NMR spectrum, characteristic peaks are shown at 169.1, 164.6, 151.8, 115.7 and 67.7, as results from the following table:

TABLE 1

X-ray diffraction spectrum of moxifloxacin hydrochloride form A, registered on a Philips PW3710 spectrometer (X-ray Diffractometer). (Cu Kα radiation, generator voltage 40 kV, slit divergence 1°, receiving slit 0.2 mm, scan mode step start angle 5.000, end angle 35.000, time per step 2.000 s)

| Angle (2 Θ) | D (Å) | Rel. Intens. (I/I$_0$) |
|---|---|---|
| 5.815 | 15.1858 | 49.8 |
| 7.220 | 12.2335 | 100.0 |
| 8.575 | 10.3032 | 86.1 |
| 10.335 | 8.5522 | 87.2 |
| 12.310 | 7.1842 | 19.4 |
| 13.200 | 6.7018 | 17.0 |
| 14.085 | 6.2826 | 16.3 |
| 14.535 | 6.0891 | 11.1 |
| 14.870 | 5.9527 | 20.6 |
| 15.185 | 5.8299 | 17.6 |
| 15.675 | 5.6487 | 1.9 |
| 16.620 | 5.3296 | 18.3 |
| 17.335 | 5.1114 | 60.1 |
| 17.850 | 4.9650 | 80.9 |
| 19.315 | 4.5916 | 53.7 |
| 19.760 | 4.4892 | 19.1 |
| 20.375 | 4.3551 | 2.5 |
| 21.640 | 4.1033 | 47.6 |
| 22.295 | 3.9842 | 12.7 |
| 23.160 | 3.8373 | 4.2 |
| 23.625 | 3.7628 | 1.9 |
| 24.705 | 3.6007 | 26.9 |
| 25.115 | 3.5428 | 17.6 |
| 25.815 | 3.4483 | 15.6 |
| 26.440 | 3.3682 | 39.4 |
| 27.365 | 3.2564 | 36.3 |
| 27.970 | 3.1874 | 17.8 |
| 28.360 | 3.1444 | 14.5 |
| 29.015 | 3.0749 | 28.2 |
| 29.965 | 2.9795 | 13.9 |
| 30.545 | 2.9243 | 4.8 |
| 31.575 | 2.8312 | 5.9 |
| 32.270 | 2.7718 | 12.2 |
| 33.900 | 2.6421 | 6.4 |

TABLE 2

Solid-state $^{13}$C-NMR absorptions of moxifloxacin hydrochloride form A (p.p.m.). Spectrum registered on Varian 400 instrument:

| 175.1 | 169.0 | 166.1 | 151.7 | 150.3 | 143.7 | 140.1 | 137.5 | 135.7 | 134.7 |
| 117.8 | 115.4 | 107.9 | 106.0 | 104.8 | 67.1 | 63.3 | 59.1 | 55.6 | 52.2 |
| 50.2 | 46.7 | 40.4 | 35.1 | 22.8 | 20.0 | 18.1 | 12.8 | 9.6 | |

Figure 5:
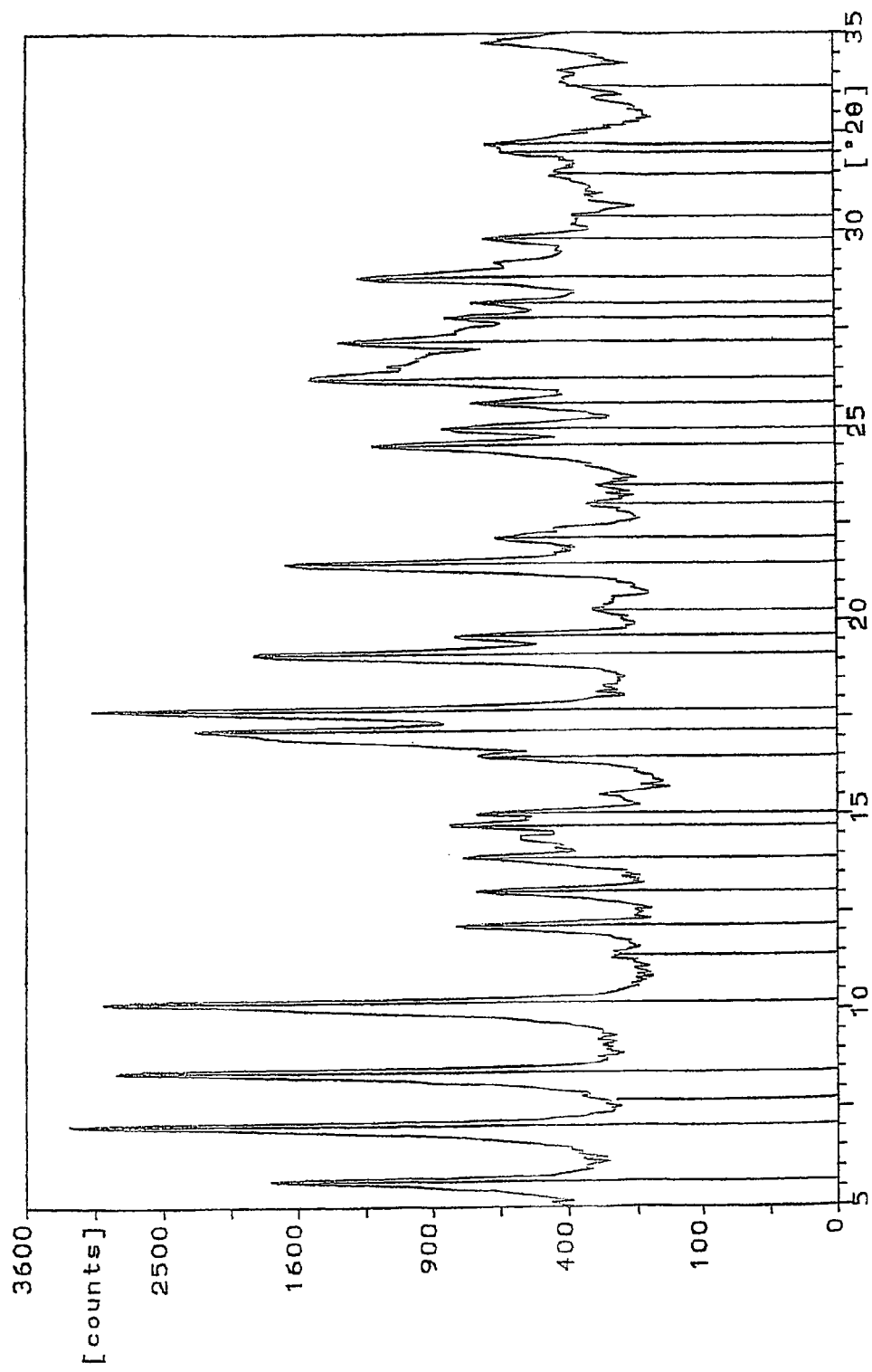
FIG. 5 is an X-ray diffraction spectrum of the crystalline form A of moxifloxacin hydrochloride after being left in air at room temperature for 5 days.

The novel crystalline form A of moxifloxacin hydrochloride is stable if left in air at room temperature for 5 days (FIG. 5); in fact it can be seen from the figure that the XRD profile does not differ substantially from the reference profile of the novel form A.

Moxifloxacin hydrochloride form A has workability and fluidity characteristics, which are optimal for formulation and does not lose these properties even after compression tests.

As previously stated, Moxifloxacin hydrochloride form B may be prepared according to the following steps:
a) suspending moxifloxacin hydrochloride in a solvent selected from alcohols and polyols or mixtures thereof, in which the resulting mixture has an overall water content of between 2.5% and 0.01% by weight,
b) heating the mixture under reflux,
c) cooling,
d) filtering the solid obtained,
e) reslurrying at reflux the solid in a solvent selected from alcohols and polyols or mixtures thereof, in which the resulting mixture has an overall water content of between 2.5% and 0.01% by weight and f) isolating the product.

In the method above described, the solvent in both the steps a) and e) is generally used in a ratio of between 50:1 and 2:1, preferably between 30:1 and 5:1, more preferably about 10:1, the ratio being expressed as ml of solvent per gram of moxifloxacin hydrochloride.

The mixture of moxifloxacin hydrochloride and solvent is kept under reflux for a variable period of time which will depend on various factors such as, for example, the type of solvent, the form of the starting product, the total quantity of water, etc., and is preferably at least 1 hour, more preferably about 4 hours.

The cooling of the mixture (step c) may be spontaneous or accelerated by appropriate means known to a person skilled in the art. The mixture may be cooled to room temperature or cooling may continue to lower temperatures; in general, it is preferred to allow the mixture to cool spontaneously until room temperature is reached.

In a particularly preferred method, cooling to room temperature takes place in about 2 hours and the mixture is allowed to rest at that temperature for a further 2 hours before the isolation (step d) is performed.

The product obtained is then filtered and charged again as wet in a reactor where a reslurry at reflux in one of the solvents as defined above is performed (step e), for a period of time ranging generally from 1 to 4 hours, preferably for about 2 hours. After cooling, the crystalline material is isolated (step f), generally by filtration, and dried under vacuum, preferably at 40° C. for 12 hours, thus obtaining moxifloxacin hydrochloride form B.

Figure 6:
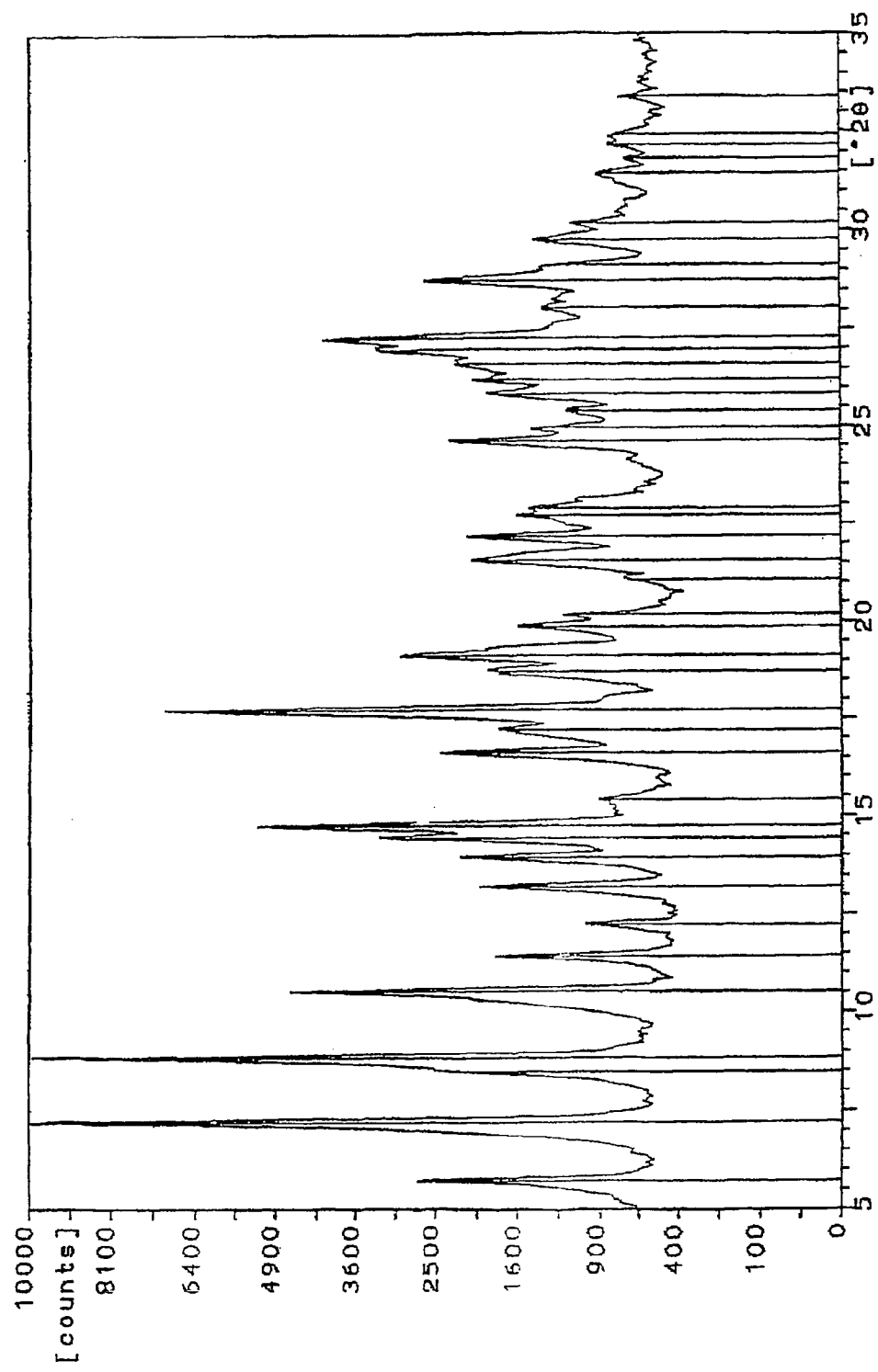
FIG. 6 is an X-ray diffraction spectrum (XRD) of the crystalline form B of moxifloxacin hydrochloride.
Figure 7:
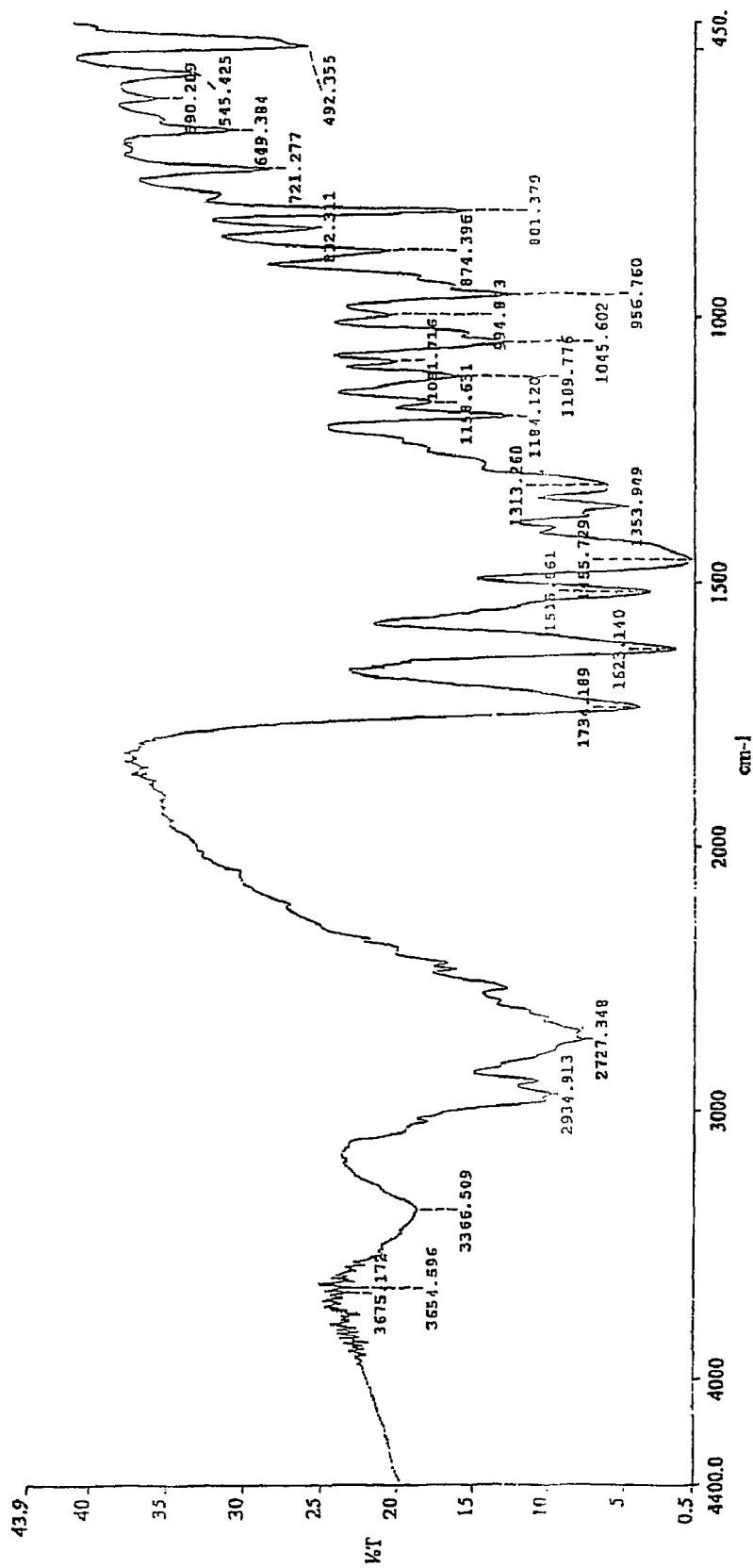
FIG. 7 is an infrared spectrum of the crystalline form B of moxifloxacin hydrochloride.
Figure 8:
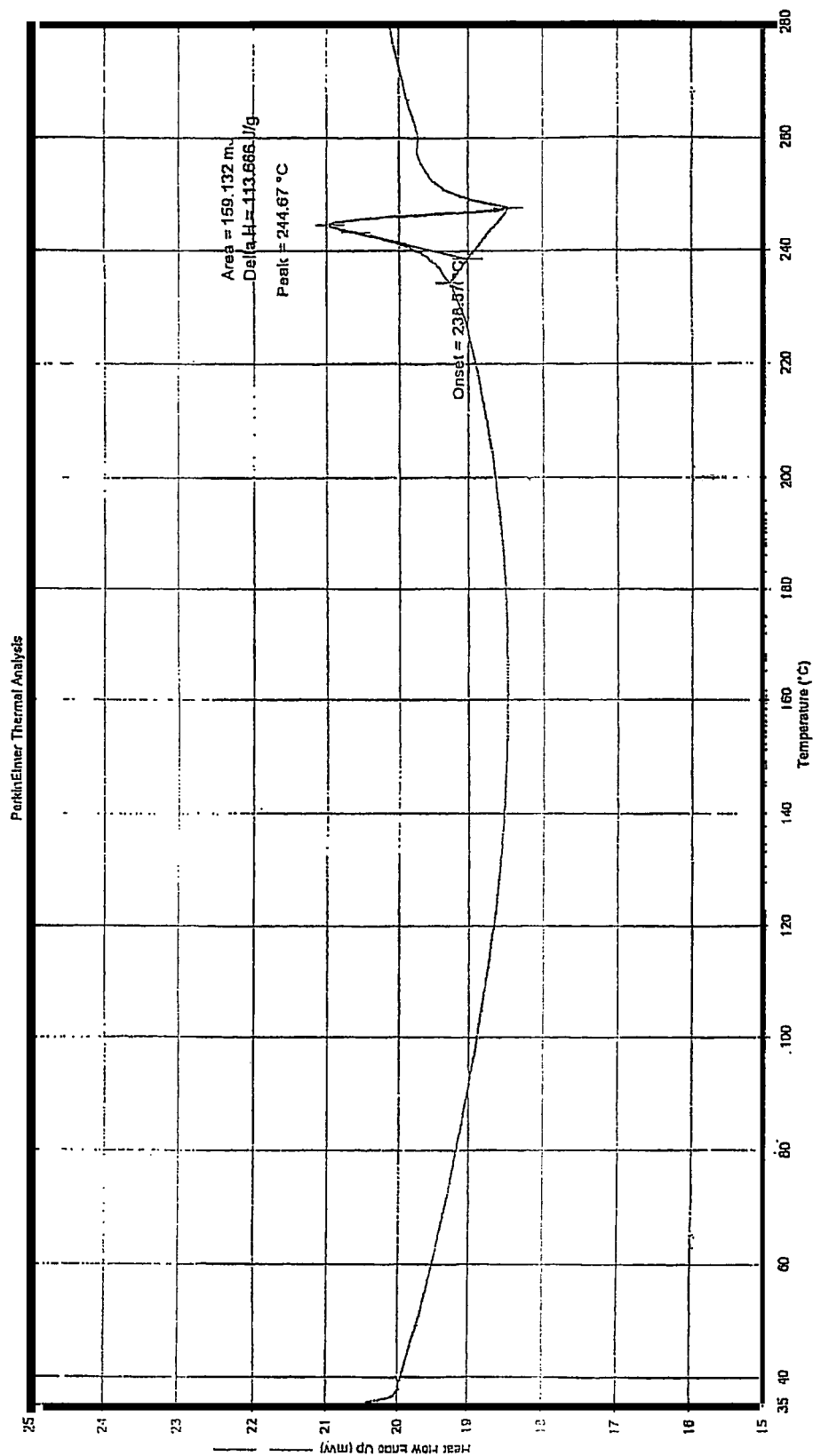
FIG. 8 is a DSC trace of the crystalline form B of moxifloxacin hydrochloride.

The novel crystalline form B of moxifloxacin hydrochloride is characterized by the X-ray diffraction spectrum (XRD) which is shown in FIG. 6 and described in Table 3, by the IR spectrum which is given in FIG. 7, and by the DSC trace which is shown in FIG. 8. The differences in comparison with the known forms can clearly be distinguished by comparing this spectral data with that of the anhydrous and monohydrate forms described in U.S. Pat. No. 5,849,752. In particular, in the XRD spectrum of the novel form B, characteristic peaks situated at 7.2, 8.8, 10.5 and 14.7 are distinguished.

TABLE 3

X-ray diffraction spectrum of moxifloxacin hydrochloride form B, registered on a Philips PW3710 spectrometer (X-ray Diffractometer). (Cu Ka radiation, generator voltage 40 kV, slit divergence 1°, receiving slit 0.2 mm, scan mode step start angle 5.000, end angle 35.000, time per step 2.000 s)

| Angle (2 Θ) | D (Å) | Rel. Intens. (I/I$_0$) |
|---|---|---|
| 5.700 | 15.4919 | 24.0 |
| 7.200 | 12.2675 | 100.0 |
| 8.470 | 10.4307 | 18.9 |
| 8.820 | 10.0176 | 91.6 |
| 10.505 | 8.4142 | 44.0 |
| 11.405 | 7.7522 | 14.6 |
| 12.220 | 7.2369 | 5.9 |
| 13.200 | 6.7018 | 16.2 |
| 13.925 | 6.3544 | 18.1 |
| 14.415 | 6.1395 | 26.6 |
| 14.740 | 6.0049 | 49.9 |
| 15.395 | 5.7508 | 4.9 |
| 16.600 | 5.3360 | 20.7 |
| 17.180 | 5.1571 | 13.7 |
| 17.705 | 5.0054 | 68.7 |
| 18.710 | 4.7387 | 13.7 |
| 19.105 | 4.6416 | 26.2 |
| 19.865 | 4.4657 | 11.8 |
| 20.155 | 4.4021 | 7.6 |
| 21.055 | 4.2159 | 2.4 |
| 21.545 | 4.1211 | 16.9 |
| 22.155 | 4.0090 | 17.3 |
| 22.690 | 3.9157 | 11.8 |
| 22.905 | 3.8794 | 10.5 |
| 24.610 | 3.6144 | 18.7 |
| 24.955 | 3.5652 | 10.0 |
| 25.385 | 3.5058 | 7.0 |
| 25.815 | 3.4483 | 14.5 |
| 26.195 | 3.3992 | 16.3 |
| 26.605 | 3.3477 | 18.4 |
| 26.960 | 3.3044 | 28.7 |
| 27.265 | 3.2681 | 37.0 |
| 28.045 | 3.1790 | 9.0 |
| 28.730 | 3.1047 | 22.2 |
| 29.110 | 3.0651 | 8.5 |
| 29.745 | 3.0011 | 9.6 |
| 30.170 | 2.9598 | 6.2 |
| 31.440 | 2.8430 | 4.1 |
| 31.795 | 2.8121 | 1.9 |
| 32.145 | 2.7823 | 3.1 |
| 32.410 | 2.7601 | 2.5 |
| 33.385 | 2.6817 | 1.8 |

The following preparation examples are now given to illustrate some of the methods that can be used to obtain the novel crystalline forms of moxifloxacin hydrochloride but they are not intended to limit the invention in any way.

EXAMPLE 1

907.4 g of moxifloxacin hydrochloride monohydrate and 9070 ml of absolute ethanol (K.F.<0.1%) were failed into a 10 liter jacketed reactor and equipped with a mechanical stirrer, reflux condenser, and thermometer. The suspension was brought to reflux with stirring and was kept in those conditions for 4 hours. The temperature was then reduced to 20° C. and the solid was filtered out and washed with 900 ml of absolute ethanol. The filtered solid was then discharged and dried under vacuum (30 mmHg) at 40° C. for 18 hours to give moxifloxacin hydrochloride form A having a water content of about 1% K.F.).

EXAMPLE 2

10 g of anhydrous moxifloxacin hydrochloride and 200 ml of ethanol with 0.3% K.F. were loaded into a 250 ml flask. The mixture was brought to reflux and kept in those conditions for 4 hours, after which it was cooled to room temperature. The solid product was filtered out and washed with 30 ml of absolute ethanol. The solid was dried under vacuum (30 mmHg) at 40° C. for 16 hours to give 8.5 g of moxifloxacin hydrochloride form A.

EXAMPLE 3

20 g of anhydrous moxifloxacin hydrochloride and 250 ml of isopropanol with 0.2% K.F. were loaded into a 500 ml flask. The mixture was brought to reflux and was kept in those conditions for 4 hours, after which it was cooled to room temperature. The solid product was filtered out and washed with 50 ml of isopropanol. The solid was dried under vacuum (30 mmHg) at 40° C. for 16 hours, to give 8.0 g of moxifloxacin hydrochloride form A.

EXAMPLE 4

10 g of anhydrous moxifloxacin hydrochloride and 200 ml of isobutanol with 0.3% K F. were loaded into a 250 ml flask. The mixture was brought to reflux and was kept in those conditions for 4 hours, after which it was cooled to room temperature. The solid product was filtered out and washed with 30 ml of absolute ethanol. The solid was dried under vacuum (30 mmHg) at 40° C. for 16 hours to give 7.8 g of moxifloxacin hydrochloride form A.

EXAMPLE 5

10 g of moxifloxacin hydrochloride monohydrate and 200 ml of 1,2-propandiol with 0.1% K.F. were loaded into a 250 ml flask. The mixture was brought to reflux and was kept in those conditions for 4 hours, after which it was cooled to room temperature. The solid product was filtered out and washed with 30 ml of absolute ethanol. The solid was dried under vacuum (30 mmHg) at 40° C. for 16 hours to give 8.2 g of moxifloxacin hydrochloride form A.

EXAMPLE 6

200 mg of moxifloxacin hydrochloride form A, 200 mg of Avicel Ph 112, and 5 mg of magnesium stearate were introduced into a mortar.

The powder was mixed and transferred into a Graseby Specac press and compressed by the application of a compression force of 5 tons. The procedure described was repeated a further 10 times, producing 10 identical tablets.

EXAMPLE 7

10 g of anhydrous moxifloxacin hydrochloride and 200 ml of ethanol with 0.3% K.F. were loaded into a 250 ml flask. The mixture was brought to reflux and kept in those conditions for 4 hours, after which it was cooled to room temperature. The solid product was filtered out and washed with 30 ml of absolute ethanol. The solid was recharged in a 250 ml flask, 200 ml of absolute ethanol with 0.1% K. F. were added and the mixture was brought to reflux and maintained in these conditions for 1 hour. Then the temperature was lowered to 25° C. and the crystalline solid was filtered and washed with absolute ethanol. After drying under vacuum (30 mmHg) at 40° C. for 16 hours 8.0 g of moxifloxacin hydrochloride form B were obtained.

EXAMPLE 8

20 g of moxifloxacin hydrochloride monohydrate and 250 ml of isopropanol with 0.2% K.F. were loaded into a 500 ml flask. The mixture was brought to reflux and was kept in those conditions for 4 hours, after which it was cooled to room temperature. The solid product was filtered and washed with 50 ml of isopropanol. The solid was recharged in a 250 ml flask, 200 ml of isopropanol with 0.1% K. F. were added and the mixture was brought to reflux and maintained in these conditions for 1 hour. Then the temperature was lowered to 25° C. and the crystalline solid was filtered and washed with isopropanol. After drying under vacuum (30 mmHg) at 40° C. for 16 hours 17.2 g of moxifloxacin hydrochloride form B were obtained.

The invention claimed is:

1. Crystalline moxifloxacin hydrochloride hydrated form A, characterized by an X-ray diffraction spectrum having the following principal peaks:

| Angle (2 θ) | D (A) | Rel. Intens. (I/I$_0$) |
|---|---|---|
| 5.815 | 15.1858 | 49.8 |
| 7.22 | 12.2335 | 100 |
| 8.575 | 10.3032 | 86.1 |
| 10.335 | 8.5522 | 87.2 |
| 12.31 | 7.1842 | 19.4 |
| 13.2 | 6.7018 | 17 |
| 14.085 | 6.2826 | 16.3 |
| 14.535 | 6.0891 | 11.1 |
| 14.87 | 5.9527 | 20.6 |
| 15.185 | 5.8299 | 17.6 |
| 15.675 | 5.6487 | 1.9 |
| 16.62 | 5.3296 | 18.3 |
| 17.335 | 5.1114 | 60.1 |
| 17.85 | 4.965 | 80.9 |
| 19.315 | 4.5916 | 53.7 |
| 19.76 | 4.4892 | 19.1 |
| 20.375 | 4.3551 | 2.5 |
| 21.64 | 4.1033 | 47.6 |
| 22.295 | 3.9842 | 12.7 |
| 23.16 | 3.8373 | 4.2 |
| 23.625 | 3.7628 | 1.9 |
| 24.705 | 3.6007 | 26.9 |
| 25.115 | 3.5428 | 17.6 |
| 25.815 | 3.4483 | 15.6 |
| 26.44 | 3.3682 | 39.4 |
| 27.365 | 3.2564 | 36.3 |
| 27.97 | 3.1874 | 17.8 |
| 28.36 | 3.1444 | 14.5 |
| 29.015 | 3.0749 | 28.2 |
| 29.965 | 2.9795 | 13.9 |
| 30.545 | 2.9243 | 4.8 |
| 31.575 | 2.8312 | 5.9 |
| 32.27 | 2.7718 | 12.2 |
| 33.9 | 2.6421 | 6.4. |

2. Crystalline moxifloxacin hydrochloride hydrated form A, characterized by an X-ray diffraction spectrum as shown in FIG. 1.

3. Crystalline moxifloxacin hydrochloride hydrated form A, characterized by a solid-state 13C-NMR spectrum as shown in FIG. 2.

4. Crystalline moxifloxacin hydrochloride hydrated form A, characterized by an IR spectrum as shown in FIG. 3.

5. A method for the preparation of crystalline moxifloxacin hydrochloride hydrated form A according to claim 1, which comprises the steps of:
   a) suspending moxifloxacin hydrochloride in a solvent selected from alcohols and polyols or mixtures thereof, in which the resulting mixture has an overall water content of between 2.5% and 0.01% by weight,
   b) heating the mixture under reflux,
   c) cooling, and
   d) isolating the product.

6. A method according to claim 5 in which the moxifloxacin hydrochloride in step a) is in anhydrous or monohydrate crystalline form.

7. A method according to claim 6 in which the moxifloxacin hydrochloride is in an anhydrous form having a water content of less than 0.3%.

8. A method according to claim 5 in which the solvent is a C1-C6 alcohol or polyol.

9. A method according to claim 5 in which the solvent has a water content of between 1% and 0.01%.

10. A method according to claim 5 in which the mixture is cooled to room temperature.

11. A method according to claim 5 in which the solvent is used in a ratio of between 50:1 and 2:1, the ratio being expressed as ml of solvent per gram of moxifloxacin hydrochloride.

12. A method according to claim 5 in which the mixture is heated under reflux for at least 1 hour.

13. A pharmaceutical composition in the form of a tablet containing crystalline moxifloxacin hydrochloride form A according to claim 1.

14. A pharmaceutical composition in the form of a tablet containing crystalline moxifloxacin hydrochloride form A according to claim 2.

15. A pharmaceutical composition in the form of a tablet containing crystalline moxifloxacin hydrochloride form A according to claim 3.

16. A pharmaceutical composition in the form of a tablet containing crystalline moxifloxacin hydrochloride form A according to claim 4.

* * * * *